United States Patent [19]

Correa et al.

[11] Patent Number: 4,565,891

[45] Date of Patent: Jan. 21, 1986

[54] OXIDATION OF TERTIARY AMINES USING OCTACYANOMOLYBDATE OR IRON (III) SALTS AS CATALYSTS

[75] Inventors: Paul E. Correa, Cincinnati, Ohio; Dennis P. Riley, Chesterfield, Mo.

[73] Assignee: The Procter & Gamble Company, Cincinnati, Ohio

[21] Appl. No.: 632,774

[22] Filed: Jul. 19, 1984

[51] Int. Cl.$^4$ ............................................. C07C 135/02
[52] U.S. Cl. .................................. 564/298; 260/404; 544/106; 544/264; 544/383; 546/127; 546/133; 546/184; 546/348; 548/542; 548/565; 562/442; 562/575
[58] Field of Search ................ 260/404; 544/106, 264, 544/383; 546/127, 133, 184, 348; 548/542, 565; 562/442, 575; 564/298

[56] References Cited

U.S. PATENT DOCUMENTS

| | | |
|---|---|---|
| 3,047,579 | 7/1962 | Witman . |
| 3,274,252 | 9/1966 | Albert et al. . |
| 3,332,999 | 7/1967 | Mitchell et al. . |
| 3,390,182 | 6/1968 | Kollar et al. . |
| 3,657,251 | 4/1972 | Smetana et al. . |
| 3,953,362 | 4/1976 | Lines et al. . |
| 4,264,776 | 4/1981 | Hershman et al. . |

FOREIGN PATENT DOCUMENTS

| | | | |
|---|---|---|---|
| EP92862 | 11/1983 | European Pat. Off. ............ | 564/298 |
| 1471967 | 3/1967 | France . | |

OTHER PUBLICATIONS

Beckwith et al., "Amine Autoxidation in Aqueous Solution," *Aust. J. Chem.*, vol. 36, (1983), pp. 719-739.
*Chem. Abs.* 97:144113q; 94:138942f; 94:163272v.
Yamamoto et al., "Diethylbis(dipyridyl)iron: A Butadiene Cyclodimerization Catalyst," *J. Am. Chem. Soc.*, vol. 90, (1968), pp. 1878-1883.
Fukuzumi et al., "Electron Transfer from Tetrakis-(isocyanide)rhodium(I) Monomers and the Oligomers to Iron (III) and Cobalt (III) Complexes. Enhancement of the Reactivity by the Oligomerization," *Bull. Chem. Soc. Jpn.*, vol. 55, (1982), 3482-90.
*Chem. Abs.* 75:151598a.
Sheng et al., "Hydroperoxide Oxidations Catalyzed by Metals: The Oxidation of Tertiary Amines to Amine Oxides," *J. Org. Chem.*, vol. 33, (1968), pp. 588-590.
*Chem. Abs.* 66:10891y.

*Primary Examiner*—Robert V. Hines
*Attorney, Agent, or Firm*—Eric W. Guttag; Steven J. Goldstein; Richard C. Witte

[57] ABSTRACT

A process for the catalytic oxidation of nonaromatic tertiary amines to the respective amine oxides is disclosed. An aqueous solvent system containing the tertiary amine is formed with an initial pH about equal to or greater than the pKa of the tertiary amine. This aqueous system is contacted with gaseous molecular oxygen at an oxygen partial pressure of at least about 50 psi and a temperature of at least about 80° C. in the presence of certain octacyanomolybdate or iron (III) salts. The resulting oxidation converts the tertiary amine to the respective amine oxide in good yield.

28 Claims, No Drawings

OXIDATION OF TERTIARY AMINES USING OCTACYANOMOLYBDATE OR IRON (III) SALTS AS CATALYSTS

TECHNICAL FIELD

The present application relates to the preparation of amine oxides, especially detergent amine oxides, by the oxidation of nonaromatic tertiary amines with molecular oxygen using certain octacyanomolybdate or iron (III) salts as catalysts.

Amine oxides have a number of different uses. For example, amine oxides prepared from aromatic and nonaromatic tertiary amines can be used as light duty liquid detergents, pour point depressants and polymerization inhibitors. See U.S. Pat. No. 3,657,251 to Smetana, issued Apr. 18, 1972. Amine oxides have also been used in other areas such as the drug field. See U.S. Pat. No. 3,520,888 to Johnston, issued July 21, 1970, which discloses 1,2,3,4-tetrahydrophenazine-5,10-dioxides useful in controlling chronic respiratory disease in poultry and in promoting and improving feed efficiency of animals in general.

Of particular importance to the present application is the use of detergent amine oxides as low temperature body soil removal agents. Such amine oxides are usually derived from trialkyl tertiary amines or monoalkylalkylene oxide dialkyl tertiary amines. One of the alkyl groups (or the monoalkylalkylene oxide group) has a relatively long carbon chain (e.g., $C_{10}-C_{18}$) while the remaining two alkyl groups have relatively short carbon chains (e.g., $C_1-C_4$). See, for example, U.S. Pat. No. 4,276,205 to Ferry, issued June 30, 1981 (amine oxides derived from trialkyl or monoalkylalkylene oxide dialkyl tertiary amines suitable for cool or cold water detergents); U.S. Pat. No. 3,843,563 to Davies et al., issued Oct. 22, 1974 (detergent composition containing amine oxides derived from trialkyl tertiary amines); U.S. Pat. No. 3,341,459 to Davis, issued Sept. 12, 1967 (amine oxides derived from alkylpolyethoxy dialkyl tertiary amines suitable for cool water detergent compositions).

Amine oxides can be prepared by oxidation of the respective tertiary amines with a strong oxidizing agent. The preferred oxidizing agent used is hydrogen peroxide. A dilute, or preferably concentrated (30% or greater) hydrogen peroxide solution is added in a stoichiometric or greater amount to an aqueous solution containing the tertiary amine for conversion thereof to the amine oxide. See, for example, U.S. Pat. No. 3,215,741 to Chadwick, issued Nov. 2, 1965. The yields and reaction rate can be improved by incorporation of catalysts and/or chelating agents. See U.S. Pat. No. 3,333,000 to Albert et al., issued July 25, 1967 (mixture of an alkali metal carbonate and an alkali metal polyphosphate as the catalyst); U.S. Pat. No. 4,247,480 to Murata et al., issued Jan. 27, 1981 (carbon dioxide as the catalyst); U.S. Pat. No. 3,283,007 to Chadwick, issued Nov. 1, 1966 (diethylenetriaminepentaacetic acid as the chelating agent). Other oxidizing agents such as the peroxy acids and ozone have also been used to oxidize tertiary amines to the respective amine oxides. See, for example, U.S. Pat. No. 3,520,888 to Johnston, issued July 21, 1970 (oxidation of 1,2,3,4-tetrahydrophenazines to the respective 5,10-dioxides using peracetic acid, perbenzoic acid, m-chloroperbenzoic acid, performic acid or monoperphthalic acid); U.S. Pat. No. 3,657,251 to Smetana, issued Apr. 18, 1972 (oxidation of tertiary amines to amine oxides using an ozone derivative in the presence of a molybdenum, tungsten or vanadium oxide forming catalyst; oxidation of tertiary amines to amine oxides using peracetic acid, perbenzoic acid and monoperphthalic acid also disclosed).

The primary process for preparing detergent amine oxides is by oxidation of the respective tertiary amines with hydrogen peroxide. However, the use of hydrogen peroxide as an oxidizing agent has a number of significant disadvantages. Compared to oxygen, hydrogen peroxide is a relatively expensive oxidizing agent. Also, as with any strong oxidizing agent, hydrogen peroxide requires special handling. Further, the oxidation of longer chain alkyl tertiary amines by hydrogen peroxide can cause gel formation problems unless the hydrogen peroxide concentration is dilute, the reaction temperature is controlled, salts are added to the reaction mixture, or the reaction mixture is diluted with water during the course of the reaction. See U.S. Pat. No. 3,432,555 to Mahnken, issued Mar. 11, 1969 (column 1, line 39 to column 2, line 40); U.S. Pat. No. 3,463,817 to Mahnken, issued Aug. 26, 1969 (column 2, line 43 to column 2, line 66); U.S. Pat. No. 3,215,741 to Chadwick, issued Nov. 2, 1965 (column 1, line 39 to column 2, line 22).

European Patent Application No. 92,862 to Riley et al., published Nov. 2, 1983, discloses the preparation of detergent amine oxides from tertiary amines using oxygen. In this process, an aqueous solvent system containing the tertiary amine is contacted with gaseous molecular oxygen at an oxygen partial pressure of at least about 50 psi and a temperature of at least about 80° C. Oxidation of the amine to the respective amine oxide is fairly slow. Reaction times of up to 64 hours are typically required to obtain a high yield (80% or better) of amine oxide in this non-catalyzed process. Accordingly, it would be desirable to find a catalyst which would accelerate this oxidation reaction.

BACKGROUND ART

A. Catalyzed Oxidations of Tertiary Amines

Beckwith et al., "Amine Autoxidation in Aqueous Solution," *Aust. J. Chem.*, Vol. 36, (1983), pp. 719–39, discloses the autoxidation of various tertiary amines, including N-methylpyrolidine, N-methylpyridine, N-methylmorpholine, and N-dimethylbenzylamine in dimethylsulfoxide at 55° C. for 0.5 hours catalyzed by the sodium salt of 1,2-naphthaquinone-4-sulfonic acid. Uncatalyzed autooxidations of various tertiary amines including N-methylpyrrolidine, N-methylpyridine, and N-dimethylbenzylamine in water at 55° C. are also disclosed.

U.S. Pat. No. 4,264,776 to Hershman et al., issued Apr. 28, 1981, discloses the oxidation of tertiary amines in the presence of an activated carbon catalyst to prepare secondary amines. Temperatures employed are preferably in the range of from about 75° to about 150° C., with preferred oxygen partial pressures of from about 2 to about 7 $kg/cm^2$ (about 30 to about 100 psi). This oxidation reaction can be carried out in water, i.e. an aqueous solvent system, over a wide range of pH, e.g. from 1 to 10 or so. In some instances, amine oxides are obtained along with the desired secondary amines (see column 11, lines 2–6). See Example I for 40% conversion of triethylamine to diethylamine plus an unspecified amount of triethylamine oxide.

B. Reactions involving octacyanomolybdate and tris-bypyridyl iron (III) salts

*Chem. Abs.* 97:144113q, 94:138942f, and 94:163272v, disclose the liquid phase oxidation of 1-nonene at 70° C. in the presence of various cyanomolybdate salts, including K$_4$Mo(CN)$_8$. The rate of oxidation decreased in the order K$_4$Mo(CN)$_4$>K$_4$MoO(CN)$_4$>K$_4$MoO$_2$(CN)$_4$>K$_4$Mo(CN)$_8$.

Yamamoto et al., "Diethylbis(dipyridyl)iron: A Butadiene Cyclodimerization Catalyst", *J. Am. Chem. Soc.*, Vol. 90, (1968), pp. 1878–83, discloses the dimerization of butadiene using a tris-bipyridyl iron (III) salt.

Fukuzumi et al., "Electron Transfer from Tetrakis(isocyanide)rhodium(I) Monomers, and the Oligomers to Iron (III) and Cobalt(III) Complexes: Enhancement of the Reactivity by the Oligomerization", *Bull. Chem. Soc. Jpn.*, Vol. 55, (1982), pp. 3482–90, discloses the electron transfer reactions of tetrakis(isocyanide)rhodium (I) and oligomers thereof with tris-bipyridyl iron(III).

C. Preparation of amine oxides from tertiary amines using ozone or ozone derivatives and a molybdenum catalyst U.S. Pat. No. 3,657,251 to Smetana, issued Apr. 18, 1972 discloses the selective preparation of amine oxides from tertiary amines including pyridines. The tertiary amine is contacted with an organic ozone derivative in the presence of a molybdenum, tungston or vanadium oxide forming catalyst. Suitable molybdenum catalysts include molybdenum hexacarbonyl, molybdenum trioxide and dioxide, sodium molybdate and the like.

U.S. Pat. No. 3,332,999 to Mitchell et al., issued July 25, 1967, discloses the preparation of amine oxides by the oxidation of tertiary amines with ozone in the presence of lower alcohols as a reaction medium at a temperature of from about 1° to about 40° C. The ozone is frequently used with a carrier gas such as air. A Lewis acid catalyst can be used, preferably the halides of metals such as chromium.

DISCLOSURE OF THE INVENTION

The present invention relates to a process for the catalytic oxidation of nonaromatic tertiary amines to the respective amine oxides using molecular oxygen. An aqueous solvent system containing the nonaromatic tertiary amine is provided with an initial pH about equal to or greater than the pKa of the tertiary amine. This aqueous system is contacted with molecular oxygen in the presence of a catalytic amount of a catalyst selected from (1) octacyanomolybdate salts having the formula (I):

$$(M^+)_{4-n}(Mo^{(n+4)+})(CN^-)_8 \quad\quad I$$

wherein M$^+$ is a compatible cationic group and n is 0 or 1; and (2) iron (III) salts having the formula (II):

$$[(Fe^{3+})(A)_3](X^-)_3 \quad\quad II$$

wherein A is a chelating bipyridyl group and X$^-$ is a noncoordinating anionic group. Use of these octacyanomolybdate or iron (III) salts results in fairly high yields of amine oxides in a relatively short reaction time.

A. Tertiary Amines Suitable for Conversion to Amine Oxides

The process of the present invention is suitable for the conversion of a variety of nonaromatic tertiary amines to the respective amine oxides. As used herein, the term "nonaromatic tertiary amine" refers to both noncyclic tertiary amines and nonaromatic cyclic tertiary amines. It has been found that the process of the present invention does not convert aromatic cyclic tertiary amines to the respective amine oxides. Examples of such aromatic tertiary amines include the pyridines, pyrazines, pyrroles, purines, pyrimidines and like compounds.

As used herein, the term "noncyclic tertiary amine" refers to tertiary amines having the following general formula:

wherein R$^1$, R$^2$ and R$^3$ are nonaromatic groups (e.g., alkyl), or aromatic groups which are not directly substituted on the nitrogen atom (e.g., benzyl). Noncyclic tertiary amines with aromatic groups (e.g., phenyl) which are directly substituted on the nitrogen atom are not converted by the process of the present invention to the respective amine oxides. Examples of such tertiary amines with directly substituted aromatic groups include N,N-dimethylaniline (but not N,N-dimethylbenzylamine), N,N-methylphenylaniline and like compounds.

In this general formula, R$^1$, R$^2$ and R$^3$ can all be the same substituent or can be different substituents. Examples of the former class of noncyclic tertiary amines include trimethylamine, triethylamine, tri-n-propylamine, and tri-n-butylamine. Examples of the latter class include dimethyldodecylamine and dimethyltetradecylamine.

One class of noncyclic tertiary amines for which the process of the present invention is particularly suitable are those having the following general formula:

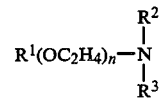

wherein R$^1$ is a C$_{10}$–C$_{22}$ (typically C$_{10}$–C$_{18}$) hydrocarbyl group and n is from 0 to about 10; and R$^2$ and R$^3$ are each a C$_1$–C$_4$ alkyl group. For the R$^1$ substituent, the hydrocarbyl group can be a straight- or branched-chain alkyl, aralkyl (e.g., benzyl), or a substituted hydrocarbyl group (e.g., hydroxyalkyl). For the R$^2$ and R$^3$ substituents, the alkyl group can be a straight- or branched-chain alkyl or substituted alkyl (e.g., hydroxyalkyl). Included within this class are the trialkyl tertiary amines or monoalkylalkylene oxide dialkyl tertiary amines which can be converted by the process of the present invention to detergent amine oxides disclosed in, for example, U.S. Pat. No. 4,276,205 to Ferry, issued June 30, 1981 (herein incorporated by reference); U.S. Pat. No. 3,843,563 to Davies et al., issued Oct. 22, 1974 (herein incorporated by reference); and U.S. Pat. No. 3,341,459 to Davis, issued Sept. 12, 1967 (herein incorporated by reference). Also included are those noncyclic tertiary amines having hydroxyalkyl groups which can be converted by the process of the present application to the detergent amine oxides disclosed in, for example, U.S. Pat. No. 3,202,714 to Zimmerer et al., issued Aug. 24, 1965 (herein incorporated by reference) and U.S. Pat. No. 3,441,611 to Drew et al., issued Apr. 29, 1969 (herein incorporated by reference). Specific examples of such tertiary amines include dimethyldodecylamine, dimethyltetradecylamine, ethylmethyltetradecylamine, dimethylcetylamine, dimethylstearylamine, ethylpropylcetylamine, diethyldodecylamine, diethyltetradecylamine, dipropyldodecylamine, bis-(2-hydroxyethyl)dodecylamine, bis-(2-hydroxyethyl)-3-dodecoxy-2-hydroxypropylamine, (2-hydroxypropyl)methyltetradecylamine, dimethyl-(2-hydroxydodecyl)amine, and the corresponding decyl, hexadecyl and octadecyl homologs of these amines. Preferred amines herein are the $C_{12}$–$C_{14}$ alkyl dimethylamines; particularly preferred is dimethyldodecylamine.

Another class of noncyclic tertiary amines for which the process of the present invention is suitable are those which can be converted to the alpha-amine oxide detergent surfactants (carboxylic acids or salts thereof having amine oxide substituents at the alpha-carbon atom) disclosed in U.S. Pat. No. 4,397,776 to Ward, issued Aug. 9, 1983 (herein incorporated by reference). These tertiary amines (hereinafter alpha-tertiary amines) have the following formula:

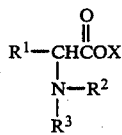

wherein $R^1$ is hydrogen or a $C_1$–$C_{20}$ hydrocarbyl group; $R^2$ and $R^3$ are each a $C_1$–$C_{20}$ alkyl group, or a $C_2$–$C_3$ alkylene oxide group having from 1 to about 10 alkylene oxide units; and X is hydrogen or a water-soluble metal, ammonium or substituted ammonium cation; the total number of carbon atoms for the hydrocarbyl and alkyl groups of $R^1$, $R^2$ and $R^3$ being from about 8 to about 36.

In the above formula, the $R^1$ hydrocarbyl group can be a straight or branched chain alkyl, alkaryl (e.g., alkyphenyl or alkylbenzyl), or a substituted hydrocarbyl group (e.g., hydroxyalkyl). The nature of $R^1$ can be varied by the selection of the parent carboxylic acid. Typical carboxylic acid starting materials include acetic acid, propionic acid, butyric acid, valeric acid, caproic acid, caprylic acid, capric acid, lauric acid, myristic acid, palmitic acid, stearic acid, eicosanoic acid, mixed coconut oil fatty acids, mixed palm oil fatty acids, mixed lard fatty acids, and mixed tallow fatty acids, which are preferred for cost considerations. $R^1$ is preferably a $C_8$–$C_{20}$ hydrocarbyl group, and most preferably a $C_{10}$–$C_{16}$ alkyl group.

The $R^2$ and $R^3$ substituents can be an alkyl group (straight or branched chain alkyl or substituted alkyl, e.g., hydroxyalkyl), or a $C_2$–$C_3$ alkylene, preferably ethylene, oxide group containing from 1 to about 10, preferably 1 to about 5, alkylene oxide units. Such a $C_2$–$C_3$ alkylene oxide group would commonly, and preferably, be terminated with a hydrogen atom, but also can be terminated with a methyl, ethyl or propyl group. $R^2$ and $R^3$ are preferably a $C_1$–$C_4$ alkyl group, and more preferably a methyl, ethyl, 2-hydroxyethyl or 2-hydroxypropyl group.

For substituent X, suitable water-soluble metal cations include any of the alkali metal (e.g. sodium, potassium) and alkaline earth metal (e.g. calcium, magnesium) cations. Useful substituted ammonium cations include, for example, the methyl-, dimethyl-, trimethyl-, diethanol- and triethanolammonium cations and quaternary ammonium cations such as tetramethylammonium and dimethyl piperidinium cations. Preferably X is a water-soluble alkali metal cation. Most preferably, X is sodium.

It will be appreciated that the above substituents are selected such that the respective amine oxides exhibit sufficient surface activity and solubility for their intended use. Thus, the total number of carbon atoms for the hydrocarbyl and alkyl groups of the $R^1$, $R^2$ and $R^3$ substituents are from about 8 to about 36, preferably from about 12 to about 26. Additionally, when $R^1$, and one of $R^2$ and $R^3$, have relatively long hydrocarbyl or alkyl chains, it is preferred that the other $R^2$ or $R^3$ be a $C_2$–$C_3$ alkylene (preferably ethylene) oxide group for optimum solubility, especially in cold water.

Another class of noncyclic tertiary amines for which the process of the present invention is suitable are those tertiary amines which can be converted to the alpha-oxyalkylene amine oxide detergent surfactants (carboxylic acids, or salts, esters or amides thereof having an oxyalkylene amine oxide substituent at the alpha-carbon atom) disclosed in U.S. Pat. No. 4,394,303 to Gosselink, issued July 19, 1983 (herein incorporated by reference). These tertiary amines (hereafter alpha-oxyalkylene tertiary amines) have the following formula:

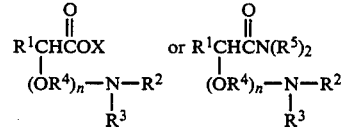

wherein $R^1$ is hydrogen or a $C_1$–$C_{20}$ hydrocarbyl group; $R^2$ and $R^3$ are each a $C_1$–$C_{20}$ alkyl group, or a $C_2$–$C_3$ alkylene oxide group having from 1 to about 10 alkylene oxide units; $R^4$ is a $C_2$–$C_6$ alkylene group; and n is from 1 to about 20; each $R^5$ is hydrogen, a $C_1$–$C_{20}$ hydrocarbyl group, or a $C_2$–$C_3$ alkylene oxide group having from 1 to about 10 alkylene oxide units; and X is hydrogen, a water-soluble metal, ammonium or substituted ammonium cation, a $C_1$–$C_8$ hydrocarbyl group, or a $C_2$–$C_3$ alkylene oxide group having from 1 to about 10 alkylene oxide units; the total number of carbon atoms for the hydrocarbyl and alkyl groups of $R^1$, $R^2$, $R^3$, and X or each $R^5$ being from about 8 to about 40.

Substituents $R^1$, $R^2$, $R^3$ or X of these alpha-oxyalkylene tertiary amines can be varied similar to the $R^1$, $R^2$ $R^3$ and X substituents, respectively, of the alpha-tertiary amines. In addition to hydrogen, each $R^5$ hydrocarbyl group can be varied similar to the $R^1$ substituent and each $R^5$ alkylene oxide group can be varied similar to the $R^2$ and $R^3$ substituents.

Substituent $R^4$ can be any $C_2$–$C_6$ alkylene group. For ease of synthesis it is preferred that $R^4$ be a $C_2$–$C_3$ alkylene group, and even more preferably an ethylene group. The number of $C_2$–$C_6$ alkylene oxide units, n, is from 1 to about 20, preferably from 1 to about 10, and more preferably from 1 to about 3. The most preferred tertiary amines herein are those in which n equals 1, since no additional stability is obtained for the respective amine oxide when n is greater than 1.

As with the alpha-tertiary amines, it will be appreciated that the substituents for the alpha-oxyalkylene tertiary amines should be selected such that the respective alpha oxyalkylene amine oxides exhibit sufficient surface activity and solubility for their intended use. Thus, the total number of carbon atoms for the hydrocarbyl and alkyl groups of $R^1$, $R^2$, $R^3$, and X or $R^5$ substituents should be from about 8 to about 40, preferably from about 12 to about 30. Additionally, when these tertiary amines, particularly the amide derivatives, have relatively long hydrocarbyl or alkyl chains at the various substituents, it is preferred that they also contain more than one $C_2$-$C_3$ alkylene (preferably ethylene) oxide unit for optimum solubility of the respective amine oxide, especially in cold water. For example, n should be greater than 1 or one or more of the $R^2$, $R^3$, X or $R^4$ substituents should be a $C_2$-$C_3$ alkylene oxide group in such tertiary amines.

As used herein, the term "nonaromatic cyclic tertiary amine" refers to N-substituted monocyclic tertiary amines having the following general formula:

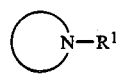

wherein $R^1$ is typically a $C_1$-$C_8$ alkyl group (e.g., alkyl, hydroxyalkyl), preferably a $C_1$-$C_4$ alkyl group and more preferably a methyl, ethyl, 2-hydroxyethyl or 2-hydroxypropyl group; and to bicyclic tertiary amines having the following general formula:

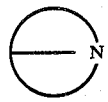

Such cyclic tertiary amines can include additional nitrogen atoms in the cyclic hydrocarbyl chain, as well as other hetero atoms such as oxygen. Examples of such cyclic tertiary amines which can be converted to the respective amine oxides by the process of the present invention include quinuclidine, N-substituted 3-pyrrolines (e.g., N-methyl-3-pyrroline), N-substituted piperidines (e.g., N-methylpiperidine), N-substituted morpholines (e.g., N-methylmorpholine), N-substituted tropines (e.g., N-methyltropine) and N,N'-substituted piperazines (e.g., N,N'-dimethylpiperazine).

B. Solvent Systems Containing Tertiary Amines

The tertiary amine to be oxidized is dissolved in an aqueous solvent system. It has been found that an aqueous environment is needed to stabilize the amine oxide formed during oxidation of the tertiary amine. It is believed that this stabilizing effect is due to the highly polar, protic nature of water as a solvent. For example, amine oxides tend to decompose in an aprotic solvent such as acetonitrile, thus significantly decreasing the yield of the amine oxide.

The concentration of the tertiary amine in the solvent system is usually dependent upon the molecular weight and solubility of the particular tertiary amine. For example, the concentration of a low-molecular weight, more soluble tertiary amine such as trimethylamine usually ranges from about 0.5 to about 2.6M. By contrast, the concentration of a higher molecular weight, less soluble tertiary amine such as dimethyldodecylamine usually ranges from about 0.2 to about 0.3M. The concentration range for the tertiary amines is typically from about 0.2 to about 3.0M. However, higher or lower concentrations can be employed consistent with the solubility of the particular tertiary amine.

For water-soluble tertiary amines such as trimethylamine, water can comprise the sole solvent of the solvent system. For other, substantially water-insoluble tertiary amines such as dimethyldodecylamine, a water-miscible solvent for the tertiary amine is used as well in the solvent system. Examples of suitable water-miscible solvents include the primary and secondary alcohols such as n-propyl alcohol, isopropyl alcohol, ethyl alcohol, and methyl alcohol. The ratio of the water-miscible solvent to water is dependent upon the particular tertiary amine and the concentration thereof in the aqueous solvent system. A weight ratio of water-miscible solvent:water of from about 1:1 to about 4:1 is usually sufficient, especially for the trialkyl tertiary amines such as triethylamine and dimethyldodecylamine.

Of particular importance to increasing the yield of amine oxide is the initial pH of the aqueous solvent system. While the pH of the solvent system throughout the reaction can be important to improving the yield of the amine oxide, the initial pH is particularly important. If the initial pH of the aqueous solvent system is too low, the nitrogen atom of the tertiary amine being oxidized tends to be protonated. Such protonation inhibits conversion of the amine to the respective amine oxide.

To provide an effective yield of the amine oxide from the respective tertiary amine, the aqueous solvent system needs to have an initial pH about equal or greater than the pKa of the particular amine. As used herein, the term "about equal to or greater than" includes a pH below the pKa of the particular amine which does not significantly inhibit the oxidation of the amine to the amine oxide. Some pKa's of trialkyl tertiary amines are as follows:

| Amine | pKa |
|---|---|
| trimethyl | 9.0 |
| triethyl | 11.0 |

The initial pH should also not be so high as to promote base-induced side reactions, in particular alpha-oxidation wherein the tertiary amine is converted to the respective secondary amine. Usually, an aqueous solvent system having an initial pH of from about 9.5 to about 12.5 is sufficient to provide conversion of trialkyl tertiary amines to the respective amine oxides in high yield. To maintain the pH of the solvent system in the desired range, a suitable buffer system can be used. Examples of suitable buffers include phosphate buffers, borate buffers and carbonate buffers. These buffers are also desirable from the standpoint of increasing the concentration of dissolved oxygen in the solvent system.

C. Octacyanomolybdate and Iron (III) Salts

One group of catalysts useful in the process of the present invention are octacyanomolybdate salts of formula (I):

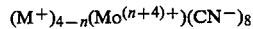

$$(M^+)_{4-n}(Mo^{(n+4)+})(CN^-)_8 \quad \text{I}$$

wherein $M^+$ is a compatible cationic group; and n is 0 or 1. Typically, the octacyanomolybdate (IV) salts (n is 0) are used in the process of the present invention.

As used herein, the term "compatible cationic group" means a positively charged moiety selected so that the octacyanomolybdate salt is soluble in the aqueous solvent system being used. When water is the sole solvent, suitable cationic groups $M^+$ include the water-soluble alkali metals such as lithium ($Li^+$) sodium ($Na^+$) and especially potassium ($K^+$), as well as ammonium ($NH_4^+$). When a water-miscible solvent such as ethyl alcohol is included as part of the solvent system, suitable cationic groups $M^+$ can include substituted ammonium cations having the following formula:

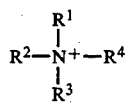

wherein $R^1$ and $R^2$ are each a $C_1$–$C_{20}$ hydrocarbyl group (e.g. alkyl, hydroxyalkyl) or together form a cyclic or heterocyclic ring of from 4 to 6 carbon atoms (e.g. piperidine, morpholine); $R^3$ is a $C_1$–$C_{20}$ hydrocarbyl group; and $R^4$ is H (quat ammonium) or a $C_1$–$C_{20}$ hydrocarbyl group (quat amine). Preferred substituted ammonium cationic groups are those where $R^4$ is H (quat ammonium); $R^1$ is $C_{10}$–$C_{18}$ alkyl, especially $C_{12}$–$C_{14}$ alkyl; and $R^2$ and $R^3$ are each $C_1$–$C_4$ alkyl, especially methyl. A particularly preferred substituted ammonium cationic group is dimethyldodecylammonium.

The octacyanomolybdate (IV) salts used in the process of the present invention are commercially available or can be prepared by art recognized methods. See Leipoldt et al., Z. Anorg. Allg. Chem., 409, (1974), pp. 343–44. In particular, the quat ammonium octacyanomolybdate salts can be prepared by acidifying the octacyanomolybdate salt in the presence of the respective tertiary amine. See Bok et al., Z. Anorg. Allg. Chem., 415, (1975), pp. 81–83. The octacyanomolybdate (V) salts can be prepared by nitric acid oxidation of the respective octacyanomolybdate (IV) salt. See Bok et al., supra.

The synthesis of specific octacyanomolybdate salts useful in the present invention is as follows:

1. Tetrapotassium octacyanomolybdate (IV).

36 g (0.15 moles) of $Na_2MoO_4.2H_2O$, 175 g of KCN (2.7 moles) and 18 g (0.33 moles) of $KBH_4$ are dissolved in 300 ml of water. During a period of 1 hour, 140 ml of concentrated acetic acid is added to the solution while stirring. The color of the solution changes from colorless to green, and finally to yellow. The solution is then heated for 20 minutes on a water bath.

After the solution is allowed to cool, 500 ml of ethanol is added to precipitate the $K_4Mo(CN)_8.2H_2O$. The product has a greenish color. The crude product is dissolved in about 150 ml of water and is boiled for about 10 minutes with animal charcoal. After the solution is filtered, 200 ml of ethanol is added to the solution to precipitate the desired clear yellow crystalline product. After one treatment with animal charcoal, pure molybdate (IV) salt is obtained.

2. Dimethyldodecylammonium octacyanomolybdate (V).

0.01 moles of $K_4Mo(CN)_3.2H_2O$ was dissolved in 20 ml of water. 25 ml of concentrated nitric acid was added in 5 ml successive portions with constant magnetic stirring after which $NO_2$ gas escaped and the orange yellow solution quickly changed color to light yellow. The solution was immediately diluted to approximately 100 ml, followed by the slow addition of slightly more than the stoichiometric quantity (0.03 moles) of dimethyldodecylamine. The precipitated molybdate (V) salt was filtered by suction and was washed three times with water.

Another group of catalysts which can be used in the process of the present invention are iron (III) salts of formula (II):

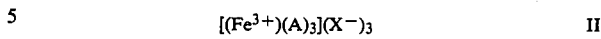

wherein A is a chelating bipyridyl group; and $X^-$ is a noncoordinating anionic group.

As used herein, the term "chelating bipyridyl group" means a polyarene group containing 2 pyridine rings which is capable of forming a bidentate ligand in a coordination complex with iron (III). Examples of suitable chelating bipyridyl groups include 2,2'-bipyridines of formula (III):

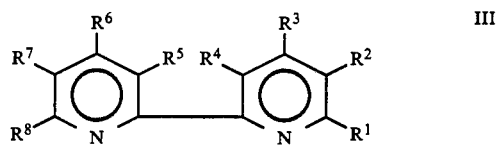

wherein $R^1$, $R^2$, $R^3$, $R^4$, $R^5$, $R^6$, $R^7$ and $R^8$ can be selected from $C_1$–$C_4$ alkyl, $C_1$–$C_4$ alkoxy, or $C_1$–$C_4$ alkyl ester groups; halogen groups (e.g. F, Cl, or Br), or hydrogen (H); or phenanthrolines of formula (IV):

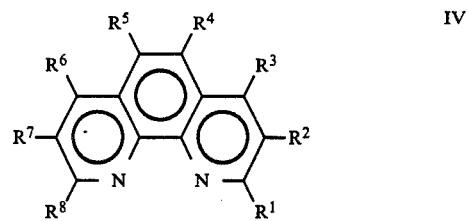

wherein $R^1$, $R^2$, $R^3$, $R^4$, $R^5$, $R^6$, $R^7$ and $R^8$ are defined as before. Preferably, $R^1$, $R^2$, $R^3$, $R^4$, $R^5$, $R^6$, $R^7$ and $R^8$ are each H. The chelating bipyridyl group 2,2'-bipyridine ($R^1$ through $R^8$ are each H) is particularly preferred.

As used herein, the term "noncoordinating anionic group" means a negatively charged moiety which does not coordinate with iron (III). Suitable noncoordinating anionic groups include $PF_6^-$, $CF_3SO_3^-$, $BF_4^-$ and $ClO_4^-$. As with the cationic group $M^+$ of the octacyanomolybdate salts, the noncoordinating anionic group should be selected so that the iron (III) salt is soluble in the aqueous solvent system. When water is used as the sole solvent, $CF_3SO_3^-$, $BF_4^-$ or $ClO_4^-$ can be used as the noncoordinating anionic group. When a water-miscible solvent such as ethyl alcohol is included as part of the solvent system, these anions plus $PF_6^-$ can be used as the noncoordinating anionic group.

The iron (III) salts used in the process of the present invention can be prepared by art recognized methods. See Burstall et al., J. Chem. Soc., (1952), p. 3578. The synthesis of one specific iron (III) salt useful in the present invention is as follows:

3. Tris-2,2'-bipyridyl iron (III)hexafluorophosphate.

Ferrous sulphate heptahydrate (1.0 g.) in distilled water (70 ml.) was treated with 36N-sulphuric acid (0.2 ml.) and 2,2'-bipyridyl (1.5 g.), and the blood-red solution was filtered. The ice-cold solution was saturated with chlorine and warmed to room temperature with a deep blue color then developing. More chlorine was passed in to ensure complete oxidation and an excess of a 30% sodium hexafluorophosphate solution was then added. The solution was allowed to cool in ice. Blue-green crystals of the phosphate were formed; these were filtered off, well washed with distilled water, and dried in vacuo.

A catalytic amount of the octacyanomolybdate or iron (III) salt is used in the process of the present invention. What is "a catalytic amount" can vary depending upon the type of salt being used, the tertiary amine being oxidized, the particular reaction conditions during oxidation (e.g., temperature), and like factors. An amount of from about 0.5 to about 20 mole percent is usually suitable for oxidation. However, an amount of from about 2 to about 10 mole percent typically provides optimum oxidation of the tertiary amine to the amine oxide. As used herein, mole percentages given for the octacyanomolybdate or iron (III) salt are based on the amount of the tertiary amine being oxidized.

D. Reaction Conditions During Oxidation

In order to prepare amine oxides according to the process of the present invention, the aqueous solvent system containing the tertiary amine and the octacyanomolybdate or iron (III) salt catalyst is contacted with molecular oxygen. Several sources of molecular oxygen can be employed. For example, air can be used in the process of the present invention. Also, substantially pure oxygen can be used.

An important parameter during this contacting step is the oxygen partial pressure. The oxygen partial pressure needs to be sufficient to insure that the concentration of molecular oxygen in the aqueous solvent system is high enough to permit oxidation of the tertiary amine to the respective amine oxide. An oxygen partial pressure of at least about 50 psi has been found sufficient for this purpose. Usually, the partial pressure is at least about 200 psi, and is preferably at least about 500 psi with a range of from about 500 to about 1500 psi being typical. Generally, the higher the oxygen partial pressure, the greater will be the yield of amine oxide in a shorter reaction time.

Another important parameter during this contacting step is the temperature. The temperature needs to be high enough to provide sufficient activation energy to initiate the catalyzed oxidation of the tertiary amine. For this purpose, a temperature of at least about 80° C. has been found to be sufficient to provide effective oxidation of the tertiary amine by molecular oxygen using octacyanomolybdate or iron (III) salts as catalysts. In batch reactions, temperatures above about 150° C. cause the formation of other reaction products over time due to decomposition of the amine oxide, particularly if it is relatively unstable. Preferably, the temperature for batch reactions is in the range of from about 100° to about 120° C. For continuous reaction systems, e.g., plug flow, temperatures above about 150° C. can be used due to the short time during which the amine oxide is subjected to such high temperatures.

The oxidation of tertiary amines to the respective amine oxides using molecular oxygen according to the process of the present invention can be carried out in a number of different batch reaction systems. An example of one such system is an autoclave (pressure bomb) which can be rocked to provide agitation. The aqueous solvent system containing the tertiary amine, any additional water-miscible solvent and the octacyanomolybdate or iron (III) salt catalyst is poured into the batch reactor. The reactor is then opened to admit gaseous molecular oxygen from a source thereof, usually a compressed gas cylinder. The reactor is then pressurized to the appropriate oxygen partial pressure and heated to the appropriate temperature. The reactor is then allowed to run with agitation to insure adequate contact between the oxygen and solvent system until the tertiary amine is converted to the amine oxide in an appropriate yield.

The process of the present invention can also be carried out in a continuous reaction system, e.g., plug flow type. In such a system, gaseous molecular oxygen as one reactant, and the solvent system containing the tertiary amine and the octacyanomolybdate or iron (III) salt catalyst as the other reactant, are continuously admitted to a reaction chamber, usually in the form of a pipe. In this reaction chamber, the oxygen contacts the solvent system at the appropriate oxygen partial pressure and the appropriate temperature. The reaction mixture is then cooled at some point in the reaction chamber to quench the reaction. Such a system permits higher temperatures to be used which results in faster oxidation of the tertiary amine to the respective amine oxide. Also, the amine oxides, especially those which are relatively unstable, can be recovered before decomposition due to heat.

After the tertiary amine has been converted to the respective amine oxide in the appropriate yield, the amine oxide can be recovered from the aqueous solvent system by standard techniques. For example, the aqueous solvent system can be stripped away to recover the amine oxide. Activated carbon can also be added to the reaction mixture to remove other trace reaction products. If desired, the amine oxide can be recrystallized to increase the purity thereof.

Specific Illustrations of the Catalyzed Oxidation of Tertiary Amines to Amine Oxides with Molecular Oxygen The following examples of the catalyzed oxidation of tertiary amines to amine oxides with molecular oxygen are used to illustrate the process of the present invention:

All oxidations were carried out in a 0.5 liter stainless steel autoclave having a glass liner. The solvent system containing distilled water, the particular tertiary amine, any additional water-miscible solvent, and a selected amount of octacyanomolybdate or iron (III) salt catalyst were poured into the autoclave. The autoclave was then charged with pure oxygen from a compressed gas cylinder. The autoclave was then pressurized and heated to the appropriate oxygen partial pressure and temperature, respectively. The autoclave was rocked to insure adequate contact between the oxygen and the solvent system. The reaction was allowed to run for the desired time. The amine oxide was recovered by stripping away the solvent system. The yield of amine oxide was determined by reverse phase high pressure liquid chromatography.

The results from the oxidation of tertiary amines using different octacyanomolybdate or iron (III) salts as catalysts (5 mole %) at 1000 psi oxygen pressure are shown in the following table:

TABLE I

| Catalyst | Temperature (°C.) | Time (hrs) | Tertiary Amine (Solvent) | Amine Oxide Yield (mole %) |
|---|---|---|---|---|
| $K_4Mo(CN)_8$ | 119 | 1 | $NMe_3(H_2O)$ | 50 |
| $K_4Mo(CN)_8$ | 126 | 3.2 | $C_{12}NMe_2$ (4:1 MeOH/$H_2O$) | 31 |

TABLE I-continued

| Catalyst | Temperature (°C.) | Time (hrs) | Tertiary Amine (Solvent) | Amine Oxide Yield (mole %) |
|---|---|---|---|---|
| K₄Mo(CN)₈ | 122 | 3 | C₁₂NMe₂ (4:1 MeOH/H₂O) | 36 |
| K₃Mo(CN)₈ | 130 | 3 | C₁₂NMe₂ (4:1 MeOH/H₂O) | 45 |
| K₃Mo(CN)₈ | 108 | 5.75 | C₁₂NMe₂ (4:1 MeOH/H₂O) | 38** |
| K₃Mo(CN)₈ | 96 | 2.5 | C₁₂NMe₂ (4:1 MeOH/H₂O) | 11 |
| Fe(bipyr*)₃(PF₆) | 109 | 4.5 | C₁₂NMe₂ (EtOH/H₂O)) | 52 |

*bipyr = 2,2'-bipyridine
**1500 psi O₂ pressure

What is claimed is:

1. A process for the catalytic oxidation of a nonaromatic tertiary amine to the respective amine oxide, which comprises the steps of:
   (a) providing an aqueous solvent system containing a nonaromatic tertiary amine, the aqueous solvent system having an initial pH about equal to or greater than the pKa of the tertiary amine; and
   (b) contacting the aqueous solvent system with molecular oxygen in the presence of a catalytic amount of a catalyst selected from the group consisting of: (1) octacyanomolybdate salts having the formula (I):

$$(M^+)_{4-n}(Mo^{(n+4)+})(CN^-)_8 \quad \text{I}$$

wherein M is a compatible cationic group; and n is 0 or 1; and (2) iron (III) salts having the formula (II):

$$[(Fe^{3+})(A)_3](A^-)_3 \quad \text{II}$$

wherein A is chelating bipyridyl group and $A^-$ is a noncoordinating anionic group, to oxidize the tertiary amine to the respective amine oxide.

2. A process according to claim 1 wherein the catalyst is an octacyanomolybdate salt.

3. A process according to claim 2 wherein n is 0.

4. A process according to claim 3 wherein $M^+$ is selected from the group consisting of alkali metal, ammonium and substituted ammonium cations.

5. A process according to claim 1 wherein the catalyst is an iron (III) salt.

6. A process according to claim 5 wherein A is selected from the group consisting of 2,2'-bipyridines and phenanthrolines.

7. A process according to claim 6 wherein A is 2,2'-bipyridine.

8. A process according to claim 6 wherein $X^-$ is selected from the group consisting of $PF_6^-$, $CF_3SO_3^-$, $BF_4^-$ and $ClO_4^-$.

9. A process according to claim 1 wherein the amount of the catalyst is from about 0.5 to about 20 mole percent.

10. A process according to claim 9 wherein the amount of the catalyst is from about 2 to about 10 mole percent.

11. A process according to claim 1 wherein the oxygen pressure during said contacting step is at least about 50 psi.

12. A process according to claim 11 wherein the partial pressure during said contacting step is at least about 200 psi.

13. A process according to claim 12 wherein the partial pressure during said contacting step is at least about 500 psi.

14. A process according to claim 12 wherein the temperature during said contacting step is at least about 80° C.

15. A process according to claim 14 wherein the temperature during said contacting step is from about 80° to about 150° C.

16. A process according to claim 15 wherein the temperature during said contacting step is from about 100° to about 120° C.

17. A process according to claim 14 wherein the concentration of the tertiary amine in the aqueous solvent system prior to said contacting step is from about 0.2 to about 3.0M.

18. A process according to claim 14 wherein the initial pH is from about 9.5 to about 12.5.

19. A process according to claim 14 wherein the aqueous solvent system is contacted with air.

20. A process according to claim 14 wherein the aqueous solvent system is contacted with substantially pure oxygen.

21. A process according to claim 14 wherein the aqueous solvent system further comprises a water-miscible solvent for the tertiary amine.

22. A process according to claim 21 wherein the water-miscible solvent is selected from the group consisting of methyl alcohol and ethyl alcohol.

23. A process according to claim 22 wherein the weight ratio of water-miscible solvent to water is from about 1:1 to about 4:1.

24. A process according to claim 1 wherein the tertiary amine is a noncyclic tertiary amine.

25. A process according to claim 24 wherein the noncyclic tertiary amine has the formula:

$$R^1(OC_2H_4)_n-\underset{\underset{R^3}{|}}{\overset{\overset{R^2}{|}}{N}}$$

wherein $R^1$ is a $C_{10}$–$C_{22}$ hydrocarbyl group and n is from 0 to about 10; and $R^2$ and $R^3$ are each a $C_1$–$C_4$ alkyl group.

26. A process according to claim 25 wherein $R^1$ is a $C_{10}$–$C_{18}$ alkyl group and n is 0.

27. A process according to claim 26 wherein $R^1$ is a dodecyl group and wherein $R^2$ and $R^3$ are both methyl groups.

28. A process according to claim 24 wherein the noncyclic tertiary amine is selected from the group consisting of trimethylamine and triethylamine.

* * * * *